(12) United States Patent
Chia et al.

(10) Patent No.: US 7,465,802 B2
(45) Date of Patent: Dec. 16, 2008

(54) FACILE SYNTHESIS OF A SERIES OF LIQUID CRYSTALLINE 2-(4'-ALKYLPHENYL)-5-CYANOPYRIDINES

(75) Inventors: Win-Long Chia, Sijhih (TW); Ru-Sung Lu, Hsinchung (TW)

(73) Assignee: Fu Jen Catholic University, Taipei County (TW)

( * ) Notice: Subject to any disclaimer, the term of this patent is extended or adjusted under 35 U.S.C. 154(b) by 57 days.

(21) Appl. No.: 11/609,910

(22) Filed: Dec. 13, 2006

(65) Prior Publication Data

US 2008/0146813 A1   Jun. 19, 2008

(51) Int. Cl.
*C07D 213/84* (2006.01)
*C09K 19/34* (2006.01)

(52) U.S. Cl. .................... 546/286; 252/299.61

(58) Field of Classification Search .......... 428/1.1; 252/299.61; 546/286
See application file for complete search history.

(56) References Cited

U.S. PATENT DOCUMENTS 4,684,477 A * 8/1987 Sugimori et al. ....... 252/299.61

FOREIGN PATENT DOCUMENTS

EP          374849       *  6/1990
JP          H04-213386      8/1992
JP          05112530       *  5/1993

OTHER PUBLICATIONS

Win-Long Chia and Ru-Sung Lu, Novel synthesis and mesophase studies on a series of 2-(4-alkylphenyl)-5-cyanopyridine, Dec. 14, 2005, 1-68, Fu Jen Catholic University, Taiwan.

* cited by examiner

*Primary Examiner*—Shean C Wu
(74) *Attorney, Agent, or Firm*—Pai Patent & Trademark Law Firm; Chao-Chang David Pai (57) ABSTRACT

The invention relates to a facile synthesis of a series of 2-(4'-alkylphenyl)-5-cyanopyridine liquid crystal compounds which are represented by the following formula (I):

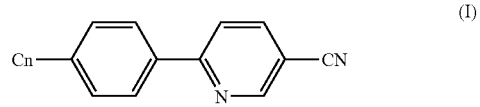

wherein $C_n$ is a linear alkyl having 1-12 carbon atoms. The synthesis of the liquid crystalline 2-(4'-alkylphenyl)-5-cyanopyridine is completed in a two-step reaction. First, a Grignard reagent (such as 4-alkylphenylmagnesium bromide) is added to a 3-cyanopyridinium salt (such as N-phenyloxycarbonyl-3-cyanopyridinium chloride) to get a 1,2-dihydropyridine. Then the 1,2-dihydropyridine is oxidized with o-chloronil to obtain the 2-(4'-alkylphenyl)-5-cyanopyridine.

4 Claims, 7 Drawing Sheets

| | |
|---|---|
| Current Date Parameters | |
| NAME | 4C-finish |
| EXPNO | 1 |
| PROCNO | 1 |
| F2 - Acquisition Parameters | |
| Date | 20050114 |
| Time | 3.47 |
| INSTRUM | spect |
| PROBHD 5mm QNP 1H/1 | |
| PULPROG | zg30 |
| TD | 16384 |
| SOLVENT | CDCl3 |
| NS | 64 |
| DS | 0 |
| SWH | 4496.403 Hz |
| FIDRES | 0.274439 Hz |
| AQ | 1.8219508 sec |
| RG | 228.1 |
| DW | 111.200 usec |
| DE | 6.50 usec |
| TE | 300.0 K |
| D1 | 1.50000000 sec |
| ==== CHANNEL f1 ==== | |
| NUC1 | 1H |
| P1 | 10.70 usec |
| PL1 | 0.00 dB |
| SFO1 | 300.1319508 MHz |
| F2 – Processing Parameters | |
| SI | 16384 |
| SF | 300.1300070 MHz |
| WDW | EM |
| SSB | 0 |
| LB | 0.10 Hz |
| GB | 0 |
| PC | 1.00 |

Current Date Parameters
NAME 4c0702
EXPNO 3
PROCNO 1
F2 - Acquisition Parameters
Date 20050703
Time 0.19
INSTRUM spect
PROBHD 5mm QNP 1H/1
PULPROG zgpg30
TD 65536
SOLVENT CDCl3
NS 602
DS 0
SWH 18832.393 Hz
FIDRES 0.287360 Hz
AQ 1.7400306 se
RG 18390.4
DW 26.550 us
DE 6.50 us
TE 300.0 K
D1 1.20000005 se
d11 0.03000000 se
d12 0.00002000 se
=== CHANNEL f1 ====
NUC1 13C
P1 9.50 us
PL1 0.00 dB
SFO1 75.4763978 MH
=== CHANNEL f2 ===
CPDPRG2 waltz16
NUC2 1H
PCPD2 90.00 us
PL2 -2.00 dB
PL12 18.50 dB
PL13 21.50 dB
SFO2 300.1313506 MH
F2 – Processing Parameters
SI 32768
SF 75.4677439 MH
WDW EM
SSB 0
LB 3.00 Hz
GB 0
PC 1.00

FACILE SYNTHESIS OF A SERIES OF LIQUID CRYSTALLINE 2-(4'-ALKYLPHENYL)-5-CYANOPYRIDINES

BACKGROUND OF THE INVENTION

1. Field of the Invention

The present invention relates to a facile synthetic method of a series of 2-(4'-alkylphenyl)-5-cyanopyridine liquid crystal compounds, and more particularly to a synthetic method which uses the Grignard reagent and promotes electrophilic properties of pyridines in the synthesis.

2. Description of the Prior Art

With the rapid development of internet, communication and computer manufacturing technologies, a variety of portable electronic products such as cellular phones, mobile computers, personal digital assistants (PDA), palm audio/visual players (e.g. MP3 and MP4 players), and the like, are playing an indispensable role in modern life. As the present electronics moves in a trend of thinner products, liquid crystal displays have been gradually taking the place of conventional cathode ray tubes. Because of their advantages in thin structure, light weight, low power consumption, low radiation contamination and compatibility with semiconductor processing technology, liquid crystal displays have found broad applications in diverse electronic products. In order to advance liquid crystal manufacturing technology, it is essential to further improve and develop liquid crystal materials.

Due to its advantages in high response speed, high resolution and wide viewing angle, the Highly Sensitive Electric Field Induced Liquid Crystal has become a common optical switching material used in the new generation of liquid crystal displays. Among the Highly Sensitive Electric Field Induced Liquid Crystals, 2-(4'-alkylphenyl)-5-cyanopyridine liquid crystal compounds are similar in molecular structure to 4-cyano-4'-pentyl biphenyl (5-CB), which has been widely used in commerce. Therefore, the former has a great potential to be used as molecular optical switches in liquid crystal displays.

Figure 1:
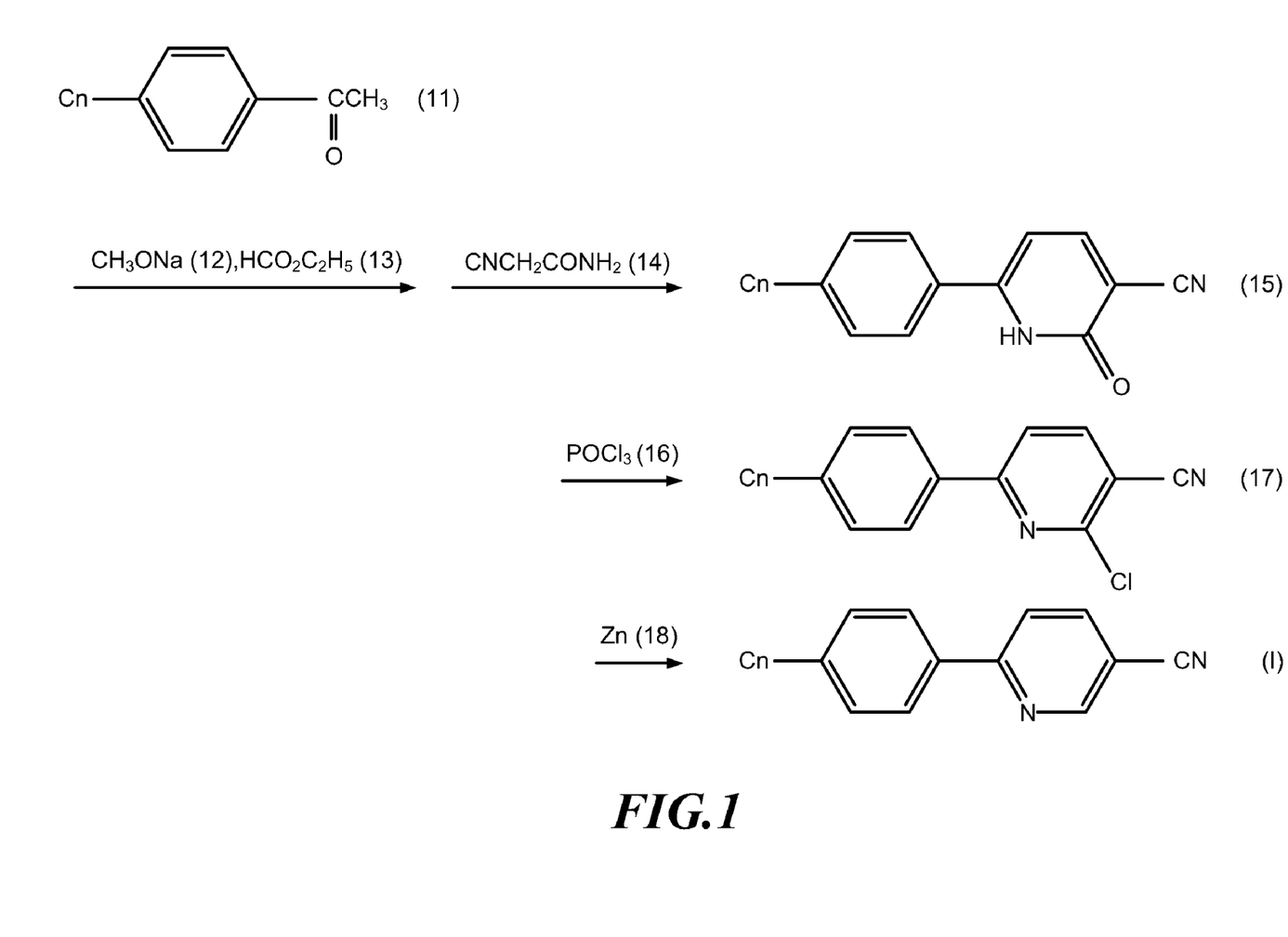
FIG. 1 shows the conventional synthetic method of 2-(4'-alkylphenyl)-5-cyanopyridine liquid crystal compounds.

Conventional synthesis of 2-(4'-alkylphenyl)-5-cyanopyridine was disclosed in JP H04-213386, as shown in FIG. 1. First, sodium methoxide $CH_3ONa$ (12), ethyl formate ($HCO_2C_2H_5$) (13) and cyanoacetamide ($CNCH_2CONH_2$) (14) are added to acetophenone (11) for cyclization (yield 38-42%) to form 2-cyano-5-(4'-alkylphenyl)pyridone (15), followed by the addition of phosphorus oxychloride ($POCl_3$) (16) for aromatization (yield 70-78%) to form 2-(4'-alkylphenyl)-5-cyano-6-chloropyridines (17). Finally, zinc (Zn) (18) is added for dechlorination (yield 39-70%) to form the liquid crystal compound (I) of 2-(4'-alkylphenyl)-5-cyanopyridines. The abovementioned synthetic method with three steps involves many procedures and consumes a large amount of reagents; moreover, some of the reagents are costly and, worst of all, the total yield is only 10-23%. For these reasons, the method is not suitable for industrial production.

Accordingly, the aforementioned synthetic method of 2-(4'-alkylphenyl)-5-cyanopyridine liquid crystal compounds still has many disadvantages and needs to be improved.

The inventor, in view of the drawbacks of said conventional synthetic method of 2-(4'-alkylphenyl)-5-cyanopyridine liquid crystal compounds, after many years of R&D on innovative improvement, has successfully developed a facile synthetic method of a series of 2-(4'-alkylphenyl)-5-cyanopyridine liquid crystal compounds.

SUMMARY OF THE INVENTION

The object of the present invention is to provide a facile synthetic method of a series of 2-(4'-alkylphenyl)-5-cyanopyridine liquid crystal compounds, which method can complete the synthesis of 2-(4'-alkylphenyl)-5-cyanopyridine liquid crystal compounds in only two steps.

The secondary object of the present invention is to provide a facile synthetic method of a series of 2-(4'-alkylphenyl)-5-cyanopyridine liquid crystal compounds with fewer procedures and increased yield when compared to the conventional synthetic method.

Figure 2:
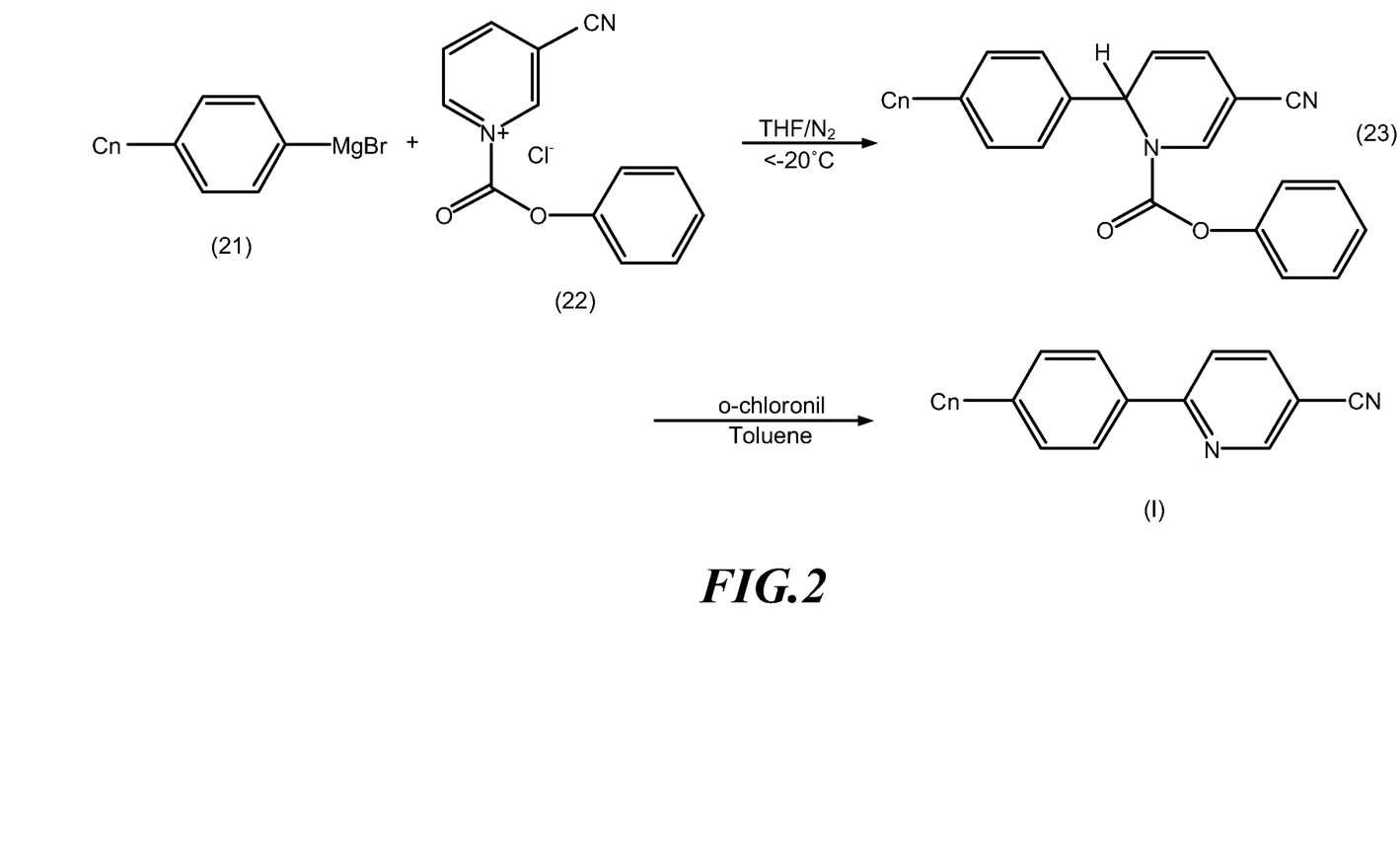
FIG. 2 shows a facile synthetic method of a series of 2-(4'-alkylphenyl)-5-cyanopyridine liquid crystal compounds of the present invention.

Referring to FIG. 2, said facile synthetic method of a series of 2-(4'-alkylphenyl)-5-cyanopyridine liquid crystal compounds achieves the aforementioned objects by way of forming pyridinium salt (22) to promote electrophilic properties of pyridine, and combining a Grignard reagent (a relatively hard base with chemical formula of RMgX, wherein X is a halogen and R is an alkylaryl group) (21) with a regioselectively attacking property, i.e., it will not attack the cyano group and other sites on the pyridine ring in the presence of pyridinium salt. First, a 1,2-dihydropyridine intermediate (23) is formed (yield 95-100%), then the 1,2-dihydropyridine intermediate (23) is oxidized to obtain the resulting liquid crystal compound (I) of 2-(4'-alkylphenyl)-5-cyanopyridine. This method not only can be completed in two steps but also has a higher throughput (yield 54-75%).

Namely, a facile synthetic method of a series of liquid crystalline 2-(4'-alkylphenyl)-5-cyanopyridine of the present invention relates to synthesis of the compounds represented by the following formula (I):

(I)

wherein $C_n$ is a linear alkyl, n=1~12.

The method comprises the following steps:

Step 1 React a Grignard reagent with N-phenyloxycarbonyl-3-cyanopyridinium chloride in a nucleophilic reaction to obtain a 1,2-dihydropyridine intermediate;

Step 2 Oxidize the 1,2-dihydropyridine intermediate with an oxidant to obtain 2-(4'-alkylphenyl)-5-cyanopyridine liquid crystal compounds, wherein said Grignard reagent is produced by adding magnesium to 4-bromoalklybenzene;

wherein said pyridinium salt is formed by adding phenyl chloroformate to 3-cyanopyridine;

wherein said oxidant is o-chloronil.

These features and advantages of the present invention will be fully understood and appreciated from the following detailed description of the accompanying Drawings.

DETAILED DESCRIPTION OF THE PREFERRED EMBODIMENT

Example 1

A Facile Synthesis of a Series of 2-(4'-alkylphenyl)-5-cyanopyridine Liquid Crystal and Its Product Analysis I. Facile Synthesis of 2-(4'-alkylphenyl)-5-cyanopyridine Liquid Crystal Add dry magnesium particles 12 millimole to 20 ml of tetrahydrofuran (THF) solution containing 10 millimole of 4-butylbromobenzene in inert gas to form a Grignard reagent of 4-alkylphenylmagnesium bromides, then gradually add the Grignard reagent to 20 ml of tetrahydrofuran (THF) solution containing 10 millimole of N-phenyloxycarbonyl-3-cyanopyridinium chloride under low temperature (−20° C.), allow the mixed solution to gradually return to ambient temperature, stir the mixed solution for 8 hours, remove the tetrahydrofuran (THF), extract the remainder with ether, rinse it twice with 10% hydrochloric acid and once with saturated saline, then dry it with magnesium sulfate to obtain 1,2-dihydropyridine intermediate. (The yield rate of said intermediate is about 95%).

Dissolve the 1,2-dihydropyridine intermediate in 20 ml dry toluene, add about 1.5 equivalent of o-chloronil to said 1,2-dihydropyridine intermediate to oxydize it, then heat the resultant solution in inert gas for a few hours under reflux, quench it with 25 ml of IN sodium hydroxide (NaOH) solution, extract with ether, then after filtering and usual aqueous phase post-treatment and separation with column chromatography, 2-(4'-alkylphenyl)-5-cyanopyridine liquid crystal compounds of formula (I) can be obtained.

(I)

wherein $C_n$ is a linear alkyl, n=1~12.

As shown in Table 1, the total yield of above two-step method is 54-75%, depending on the carbon number of the linear alkyl group.

TABLE 1

The yield of 2-(4'-alkylphenyl)-5-cyanopyridine liquid crystal compounds for the synthetic method of the present invention

| N (carbon number of straight alkyl) | Yield(%) |
|---|---|
| 4 | 75 |
| 5 | 67 |
| 6 | 63 |
| 7 | 58 |
| 8 | 54 |

II. Product Analysis

Figure 3A:
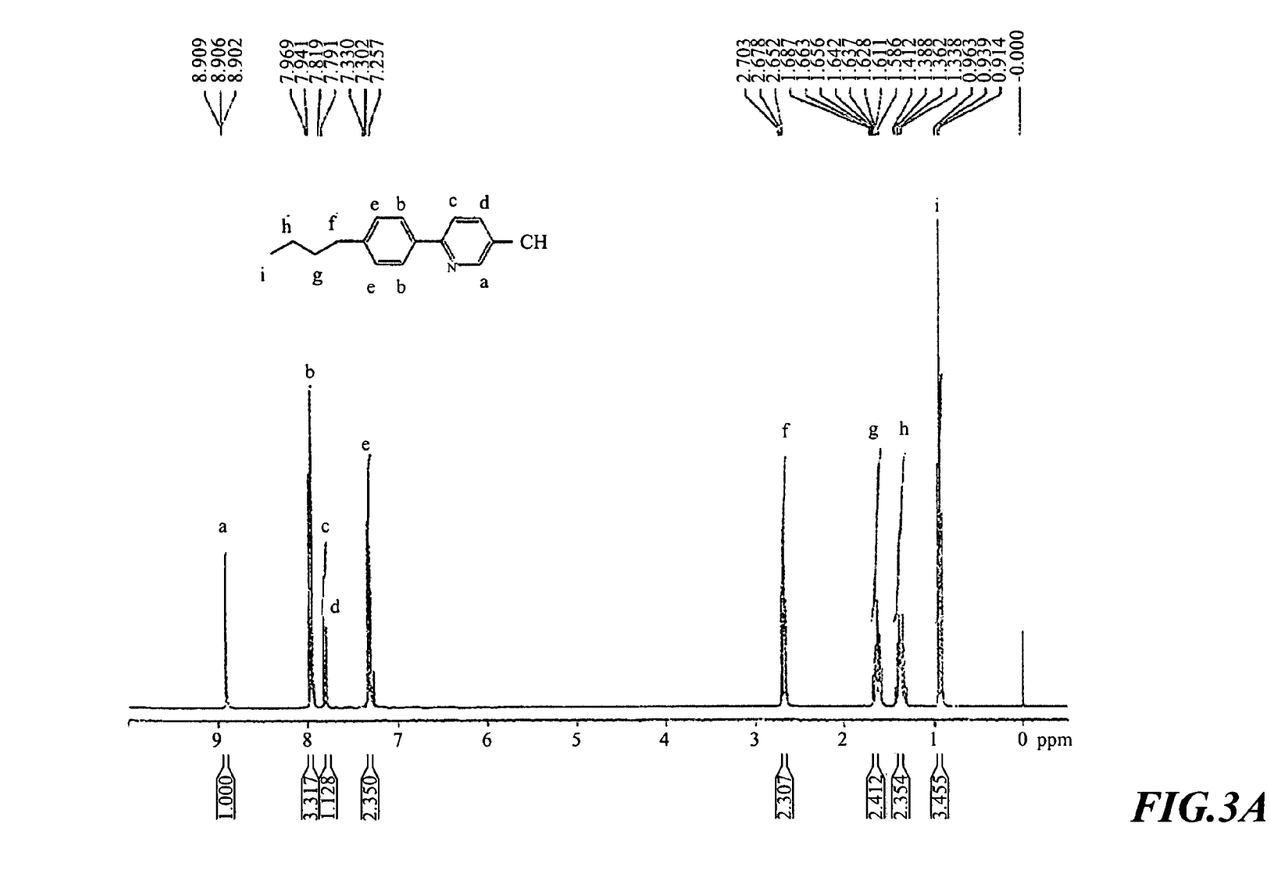
FIG. 3A is a proton magnetic resonance spectrum of 2-(4'-alkylphenyl)-5-cyanopyridine liquid crystal compounds ($C_n=4$) with corresponding current date parameters shown in FIG. 3B.
Figure 3B:
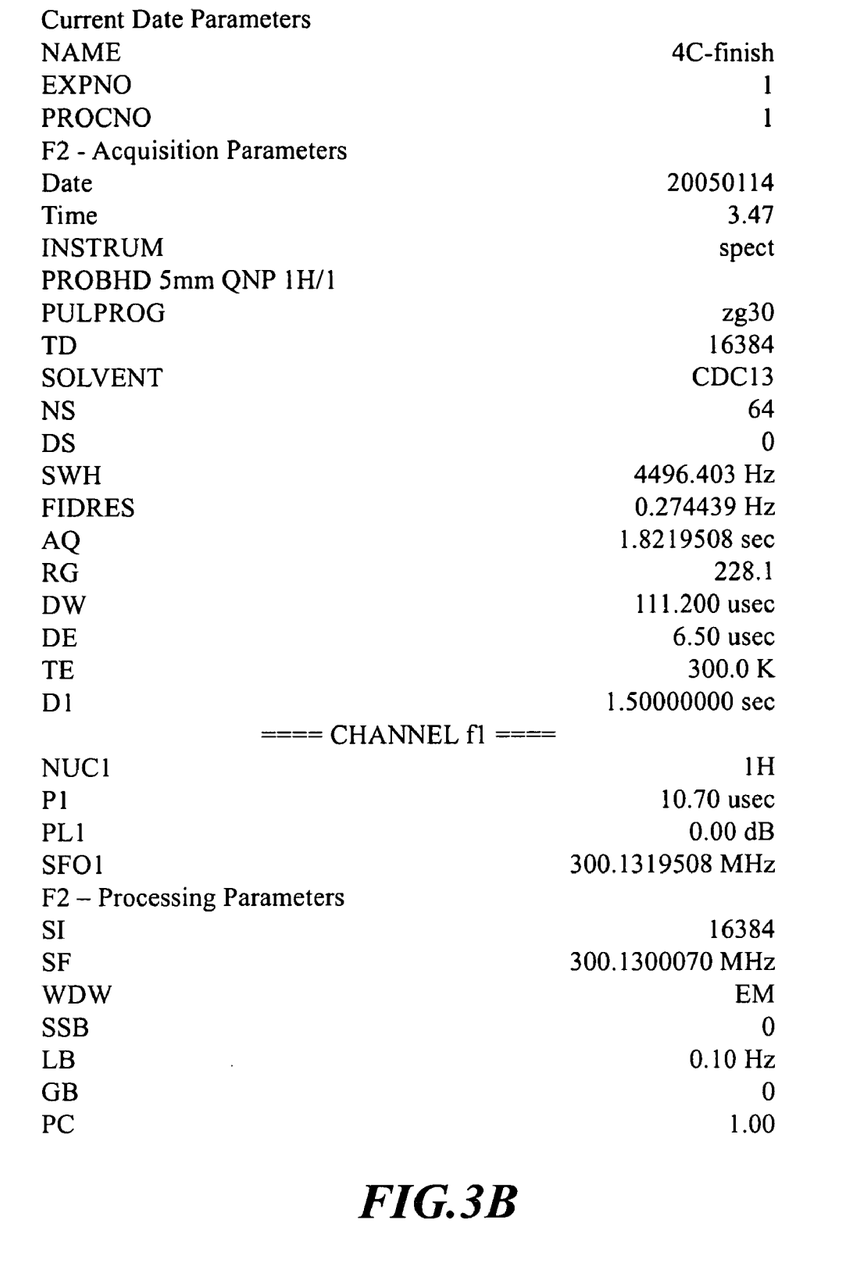
Figure 4A:
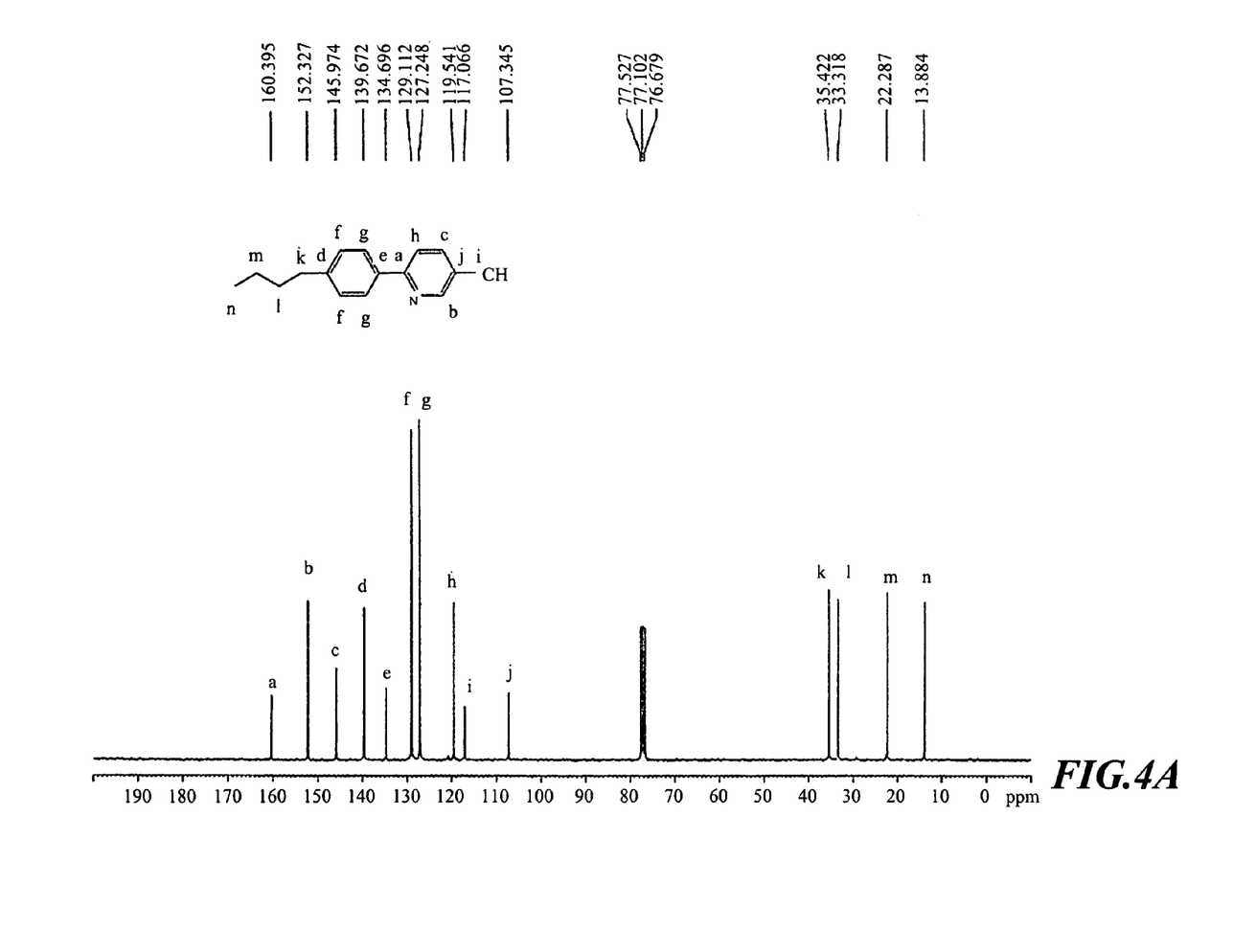
FIG. 4A is a carbon magnetic resonance spectrum of 2-(4'-alkylphenyl)-5-cyanopyridine liquid crystal compounds ($C_n=4$) with corresponding current date parameters shown in FIG. 4B.
Figure 4B:
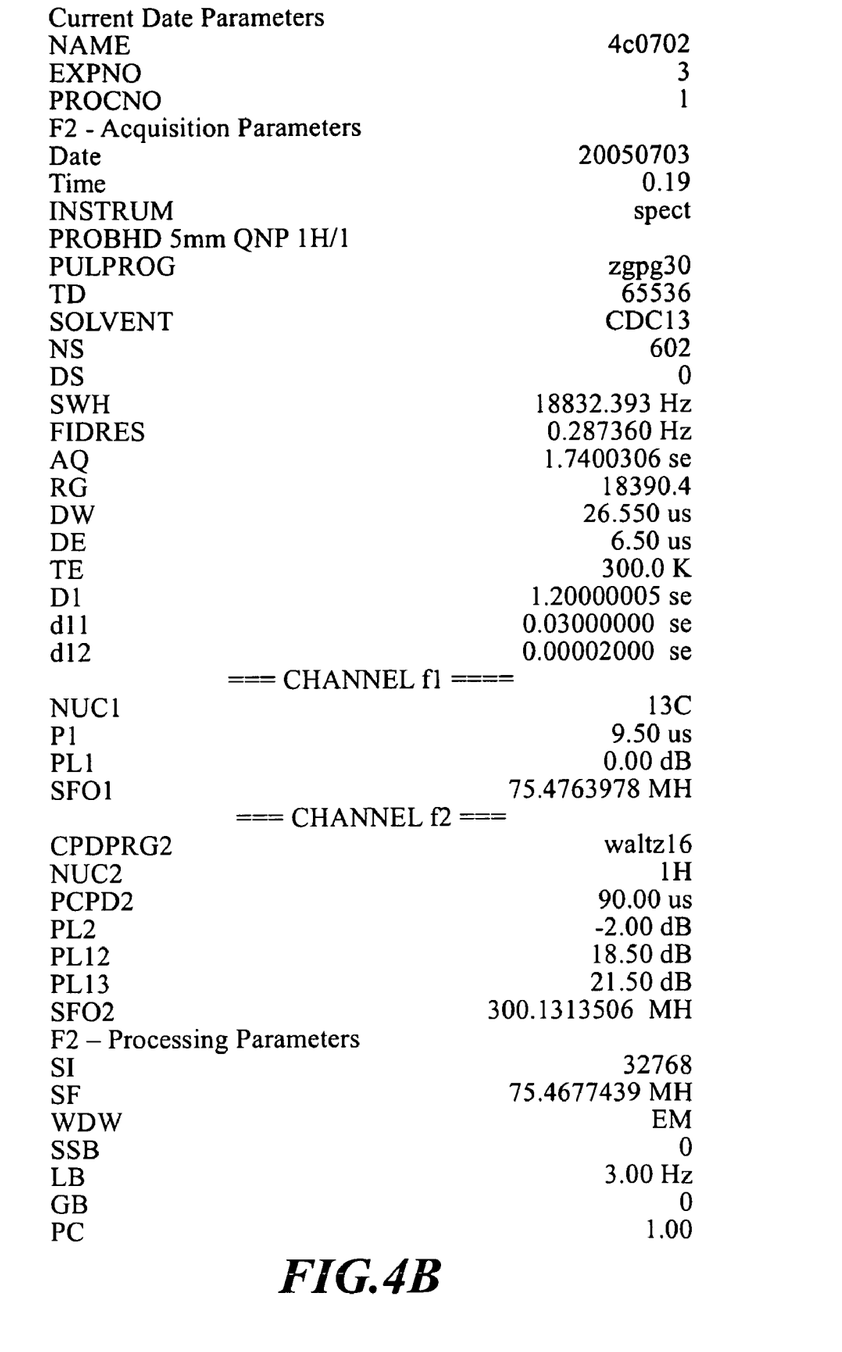

1. Analysis of 2-(4'-alkylphenyl)-5-cyanopyridine Liquid Crystal Compounds with Magnetic Resonance Spectrum Purify the 2-(4'-alkylphenyl)-5-cyanopyridine liquid crystal compounds produced by said facile synthesis: first, separate by-products with column chromatography (using a solvent of hexane: dichloromethane=2:1), then recrystallize several times with pentane or hexane under low temperature (about 5° C.). The structure of the recrystallized products is analyzed with magnetic resonance spectroscopy. For example, for 2-(4'-butylphenyl)-5-cyanopyridine liquid crystal compounds of $C_n=4$, the result is shown in FIG. 3A/FIG. 3B and FIG. 4A/FIG. 4B, wherein FIG. 3A is a proton magnetic resonance spectrum of 2-(4'-butylphenyl)-5-cyanopyridine liquid crystal compounds with corresponding current date parameters shown in FIG. 3B; and FIG. 4A is a carbon-13 magnetic resonance spectrum of 2-(4'-butylphenyl)-5-cyanopyridine liquid crystal compounds with corresponding current date parameters shown in FIG. 4B. It can be confirmed from FIGS. 3A/3B and 4A/4B that the 2-(4'-butylphenyl)-5-cyanopyridine liquid crystal compounds synthesized by the present invention has a correct structure.

Figure 5:
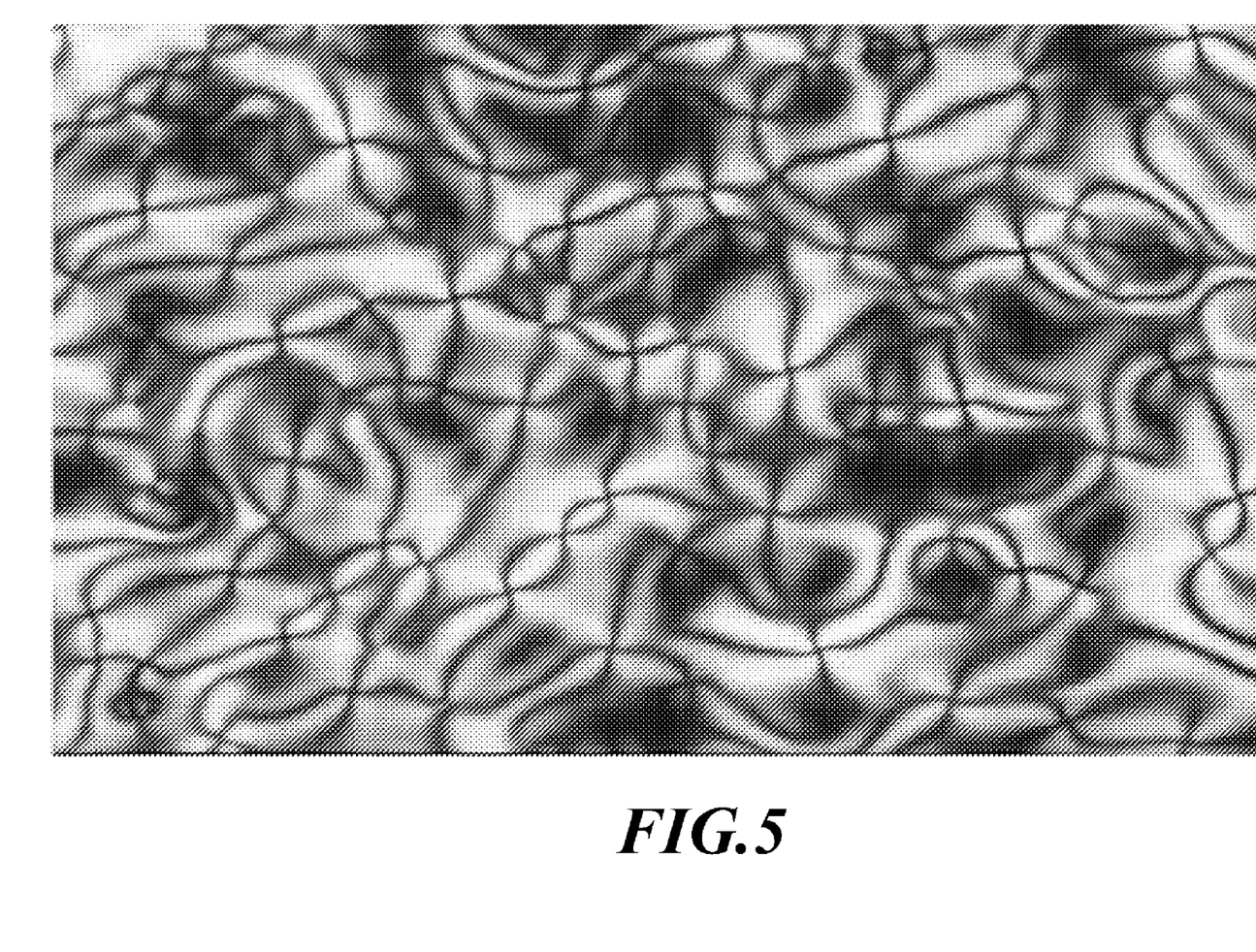
FIG. 5 shows that 2-(4'-alkylphenyl)-5-cyanopyridine liquid crystal compounds ($C_n=7$) exhibit ribbon texture when cooled from liquid phase to 65° C., as viewed under 100× polarizing optical microscope.

2. Observed Temperature Variance of 2-(4'-alkylphenyl)-5-cyanopyridine Liquid Crystal Phase The liquid crystal phase of 2-(4'-alkylphenyl)-5-cyanopyridine was observed under different temperatures. The result is shown in Table 2, wherein Cr represents crystal phase, N represents nematic phase, S represents smectic phase, and I represents isotropic phase (i.e. said liquid crystal compound is in liquid phase). As shown in Table 2, said 2-(4'-alkylphenyl)-5-cyanopyridine liquid crystal compounds produced by the present invention have excellent liquid crystal phase change under different temperatures. For example, 2-(4'-heptylphenyl)-5-cyanopyridine liquid crystal compounds of $C_n=7$ exhibits schlieren texture of nematic phase when said liquid crystal compounds are cooled from liquid phase to 65° C., as shown in FIG. 5 when it is viewed under 100× polarizing optical microscope.

TABLE 2

Phase transition of 2-(4'-alkylphenyl)-5-cyanopyridine liquid crystal compounds

| n (carbon number of straight alkyl) | Temperature Change of Liquid Crystal Phase |
|---|---|
| 4 | Cr $\xrightarrow{30°C.}$ N $\xrightarrow{55°C.}$ I $\xleftarrow{18°C.}$ $\xleftarrow{55°C.}$ |
| 5 | Cr $\xrightarrow{48°C.}$ N $\xrightarrow{68°C.}$ I $\xleftarrow{15°C.}$ $\xleftarrow{68°C.}$ |
| 6 | Cr $\xrightarrow{42°C.}$ S $\xrightarrow{48°C.}$ N $\xrightarrow{62°C.}$ I $\xleftarrow{17°C.}$ $\xleftarrow{46°C.}$ $\xleftarrow{59.5°C.}$ |
| 7 | Cr $\xrightarrow{46.5°C.}$ S $\xrightarrow{66°C.}$ N $\xrightarrow{69.7°C.}$ I $\xleftarrow{22°C.}$ $\xleftarrow{62°C.}$ $\xleftarrow{67.5°C.}$ |
| 8 | Cr $\xrightarrow{51°C.}$ S $\xrightarrow{72°C.}$ I $\xleftarrow{30°C.}$ $\xleftarrow{61°C.}$ |

3. Elemental Analysis of 2-(4'-alkylphenyl)-5-cyanopyridine Liquid Crystal Compounds Elemental analysis was performed on the abovementioned recrystallized 2-(4'-alkylphenyl)-5-cyanopyridine liquid crystal compounds and the result is shown in Table 3. It can be seen from Table 3 that the elemental ratios of 2-(4'-alkylphenyl)-5-cyanopyridine liquid crystal compounds produced by the present synthetic method are very close to the theoretical values, and the 2-(4'-alkylphenyl)-5-cyanopyridine liquid crystal compounds synthesized by the present method are of high purity.

TABLE 3

Elemental analysis of 2-(4'-alkylphenyl)-5-cyanopyridine liquid crystal compounds

| n (carbon number) of straight alkyl | Elemental Analysis |
|---|---|
| 4 | Theoretical value: C, 81.36%; H, 6.78%; N, 11.86% Analized value: C, 81.07%; H, 6.68%; N, 11.68% |
| 5 | Theoretical value: C, 81.60%; H, 7.20%; N, 11.20% Analized value: C, 81.32%; H, 7.13%; N, 11.63% |
| 6 | Theoretical value: C, 81.82%; H, 7.57%; N, 10.60% Analized value: C, 81.38%; H, 7.53%; N, 10.55% |
| 7 | Theoretical value: C, 82.01%; H, 7.91%; N, 10.07% Analized value: C, 81.41%; H, 7.82%; N, 9.87% |
| 8 | Theoretical value: C, 82.19%; H, 8.22%; N, 9.59% Analized value: C, 82.98%; H, 8.08%; N, 9.08% |

A facile synthetic method of a series of 2-(4'-alkylphenyl)-5-cyanopyridine liquid crystals provided by the present invention has the following advantages when compared to the method cited above and other conventional techniques:

1. The method provided by the present invention only needs two steps to complete the synthesis of 2-(4'-alkylphenyl)-5-cyanopyridine liquid crystal compounds, and it's one step fewer than the conventional method, which means a large amount of saving in cost and labor on commercial scale, therefore, the present method has a greater potential in industrial utilization when compared to conventional methods.

2. The total yield of 2-(4'-alkylphenyl)-5-cyanopyridine liquid crystal compounds by the present method is much more higher than that for the conventional method, therefore, the present method not only has a higher production efficiency but also can save a large amount of money on commercial scale production.

The above-stated invention was elaborated by way of examples and should not be construed to limit the scope of the invention. All equivalent embodiments or variations, for example, different Grignard reagents, different reaction times and temperatures, etc., within the spirit of the present invention should be encompassed by the appended claims.

As discussed above, the present synthesis is a novel method and more efficacious than conventional methods, it satisfies the novelty and nonobviousness requirements for a patent, therefore, the appended claims are respectfully submitted for allowance.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A facile synthetic method for synthesizing a series of 2-(4'-alkylphenyl)-5-cyanopyridine liquid crystal compounds having the following formula (I), (I)

wherein $C_n$ is a linear alkyl group, n=1~12, said synthetic method comprising the following steps:

(1) reacting a Grignard reagent with N-phenyloxycarbonyl-3-cyanopyridinium chloride in a nucleophilic reaction to obtain a 1,2-dihydropyridine intermediate; and (2) oxidizing the 1,2-dihydropyridine intermediate with an oxidant to obtain 2-(4'-alkylphenyl)-5-cyanopyridine liquid crystal compounds.

2. The facile synthetic method for synthesizing a series of 2-(4'-alkylphenyl)-5-cyanopyridine liquid crystal compounds of claim 1, wherein said Grignard reagent is produced by adding magnesium to 4-bromoalklybenzene.

3. The facile synthetic method for synthesizing a series of 2-(4'-alkylphenyl)-5-cyanopyridine liquid crystal compounds of claim 1, wherein said N-phenyloxycarbonyl-3-cyanopyridinium chloride is formed by adding phenyl chloroformate to 3-cyanopyridine.

4. The facile synthetic method for synthesizing a series of 2-(4'-alkylphenyl)-5-cyanopyridine liquid crystal compounds of claim 1, wherein said oxidant is o-chloronil.

* * * * *